(12) United States Patent
Takaki et al.

(10) Patent No.: US 10,022,331 B2
(45) Date of Patent: Jul. 17, 2018

(54) COATING AGENT FOR SOLID PREPARATION, AND FILM AND COATED SOLID PREPARATION FORMED THEREWITH

(71) Applicant: Toray Industries, Inc., Tokyo (JP)

(72) Inventors: Suguru Takaki, Kamakura (JP); Kotoe Ohta, Kamakura (JP); Yasuhide Horiuchi, Mishima (JP)

(73) Assignee: Toray Industries, Inc. (JP)

( * ) Notice: Subject to any disclaimer, the term of this patent is extended or adjusted under 35 U.S.C. 154(b) by 185 days.

(21) Appl. No.: 15/129,153

(22) PCT Filed: Mar. 31, 2015

(86) PCT No.: PCT/JP2015/060039
§ 371 (c)(1),
(2) Date: Sep. 26, 2016

(87) PCT Pub. No.: WO2015/152195
PCT Pub. Date: Oct. 8, 2015

(65) Prior Publication Data
US 2017/0105940 A1    Apr. 20, 2017

(30) Foreign Application Priority Data
Mar. 31, 2014 (JP) ................. 2014-072607

(51) Int. Cl.
*A61K 9/28* (2006.01)
*A61K 9/00* (2006.01)

(52) U.S. Cl.
CPC .......... *A61K 9/2813* (2013.01); *A61K 9/0056* (2013.01); *A61K 9/2826* (2013.01)

(58) Field of Classification Search
CPC ... A61K 9/2813; A61K 9/0056; A61K 9/2826
See application file for complete search history.

(56) References Cited

U.S. PATENT DOCUMENTS

| | | | | |
|---|---|---|---|---|
| 4,780,315 A | * | 10/1988 | Wu ........................ | A61K 9/501 424/438 |
| 8,277,844 B2 | * | 10/2012 | Noami ................ | A61K 9/2027 424/482 |
| 8,900,606 B2 | * | 12/2014 | Hayashi ............... | A61K 9/2813 424/400 |
| 2006/0127480 A1 | * | 6/2006 | Tobyn ................... | A61K 9/143 424/484 |
| 2011/0142905 A1 | * | 6/2011 | Bar-Shalom ......... | A61K 9/2846 424/423 |
| 2011/0305756 A1 | | 12/2011 | Hayashi et al. | |
| 2012/0058186 A1 | | 3/2012 | Takaki et al. | |
| 2013/0156829 A1 | | 6/2013 | Fujisaki et al. | |
| 2013/0189325 A1 | | 7/2013 | Hayashi et al. | |

FOREIGN PATENT DOCUMENTS

| | | |
|---|---|---|
| EP | 2 508 206 | 10/2012 |
| EP | 2 540 298 | 1/2013 |
| JP | 51-57814 A | 5/1976 |
| JP | 2003-125706 A | 5/2003 |
| JP | 2010-248106 A | 11/2010 |
| WO | 87/003173 A1 | 6/1987 |
| WO | 2010/074223 A1 | 7/2010 |
| WO | 2010/110018 A1 | 9/2010 |
| WO | 2010/113841 A1 | 10/2010 |
| WO | 2012/029820 A1 | 3/2012 |
| WO | 2012/147873 A1 | 11/2012 |

OTHER PUBLICATIONS

P. Van Arnum, "Advancing ODT Technology", *Pharmaceutical Technology*, vol. 31, No. 10, Oct. 2, 2007, pp. 66-76, retrieved from http://www.pharmtech.com/advancing-odt-technology.

Supplementary European Search Report dated Oct. 25, 2017, of corresponding European Application No. 15772255.4.

Okimoto, K. et al., "Generic OD Tablets (RACTAB) which Can Be Learned from Excellent Formulation Technique of Oral Rapidly Disintegrating Tablets," *The Pharmaceuticals Monthly*, 2008, vol. 50, No. 11, pp. 47-55 and a partial English translation.

* cited by examiner

*Primary Examiner* — Sean M Basquill
(74) *Attorney, Agent, or Firm* — DLA Piper LLP (US)

(57) ABSTRACT

A coating agent imparts gas barrier properties to a solid preparation while keeping rapid disintegration properties of the solid preparation, and a coating formed therewith, and provides a coated solid preparation that maintains its rapid disintegration properties and gas barrier properties, and does not generate cracks in the coating under humidified conditions. The coating agent for a solid preparation contains lactose and a swelling clay, but does not contain a water-soluble polymer, wherein the weight of the swelling clay is 20 to 50% with respect to the weight of the solid content.

18 Claims, 1 Drawing Sheet

COATING AGENT FOR SOLID PREPARATION, AND FILM AND COATED SOLID PREPARATION FORMED THEREWITH

TECHNICAL FIELD

This disclosure relates to a coating agent for a solid preparation, and a coating and a coated solid preparation formed therewith.

BACKGROUND

In recent years, orally disintegrating tablets that rapidly disintegrate in the oral cavity, are being developed as pharmaceutical formulations that can be easily taken by patients with deterioration of swallowing function due to diseases, aging, decrease in saliva production and the like.

In terms of coatings for orally disintegrating tablets, a method in which a coating agent containing a water-soluble polymer is used for an orally disintegrating tablet having not less than a certain degree of hardness, to apply a coating (JP 2010-248106 A), a method in which a coating agent composed of a polyvinyl alcohol derivative and a particular water-soluble substance is used to apply a coating (WO 2010/113841 A1), and a coating containing a particular saccharide and a water-insoluble inorganic compound or water-insoluble fatty acid (WO 2012/147873 A1), have been reported.

On the other hand, most pharmaceuticals are unstable in the presence of oxygen or water vapor, and it is known that, when pharmaceuticals are left to stand in an unpackaged state, certain changes occur in about 40% of the pharmaceuticals, causing serious problems from the viewpoint of their qualities. Thus, most commercially available pharmaceuticals, especially solid preparations, are protected against oxygen and water vapor using a packaging material such as a PTP (press through pack) sheet. In recent years, a PTP sheet having a polyvinylidene chloride laminate, which is excellent in water vapor barrier properties (moisture barrier properties) and oxygen barrier properties, has been developed, and practically used.

As methods of increasing the stability of a solid preparation in the presence of oxygen or water vapor, a method in which the solid preparation is subjected to sugar coating, and a method in which the solid preparation is subjected to film coating using a macromolecular substance, have been practically used.

The sugar coating in the former method is a coating containing sucrose as a main component, and known to have high gas barrier properties and a good external appearance. Examples of such a sugar coating that have been reported so far include a sugar coating agent containing an inorganic macromolecular substance such as montmorillonite (JP 51-57814 A) and a sugar-coated tablet prepared by coating a chewable tablet containing menthol with a sugar coating or sugarless coating (JP 2003-125706 A).

In the latter method by film coating, polyvinyl alcohol and carboxymethyl cellulose are known as macromolecular substances that exert oxygen barrier properties, and aminoalkyl methacrylate copolymer E (EUDRAGIT EPO (registered trademark), manufactured by Degussa) is known as a macromolecular substance that exerts water vapor barrier properties.

Recently, as coatings having increased gas barrier properties, a coating prepared by uniformly dispersing a high hydrogen-bonding resin and a swelling clay in a particular structure (WO 2010/074223 A1), and a coating formed with a coating agent composed of polyethylene glycol and a swelling clay (WO 2012/029820 A1), have also been reported.

However, in solid preparations, rapid disintegration properties and high tablet hardness are opposing properties. Thus, orally disintegrating tablets are insufficient in tablet hardness and high friability. Since, in such tablets, breakage or cracking occurs when they are processed in automatic packaging machines, problems in their handling in the dispensary sites have been pointed out. Moreover, since tablets are stored in the unpackaged state in automatic packaging machines, they are easily affected by storage conditions such as light, temperature, and humidity. Thus, those machines have not been applicable to drugs that are sensitive to the external environment. To solve this, for example, JP 2010-248106 A and WO 2010/113841 A1 describe giving rapid disintegration properties to coatings, and WO 2012/147873 A1 describes improvement of rapid disintegration properties as well as light-blocking properties and moisture barrier properties of coatings. In JP 2010-248106 A and WO 2010/113841 A1, however, although there are descriptions on cracking of the coatings, there is no description on moisture barrier properties of the coatings. Furthermore, in WO 2012/147873 A1, although there is a description on moisture barrier properties, nothing is disclosed about actual measurement values indicating the moisture barrier performance, and there is no description on cracking of the film.

On the other hand, one might think about attempting stabilization by blocking moisture and the like by formation of a coating having gas barrier properties using the coating agent described in WO 2010/074223 A1 or WO 2012/029820 A1. However, when a coating agent to provide gas barrier properties is applied to an orally disintegrating tablet, there is a concern that delay of disintegration due to the coating may occur so that the improvement has been difficult. Moreover, since orally disintegrating tablets are given the rapid disintegration properties by addition of a hygroscopic vehicle and a strong disintegrator, most orally disintegrating tablets increase their volumes under humidified conditions. Therefore, when an orally disintegrating tablet is to be coated, the coating needs to be given strength that is sufficient to withstand swelling of the tablet.

Thus, there is no known coating agent that realizes both rapid disintegration properties and gas barrier properties and, taking the process of water penetration into account, achievement of both properties at the same time has been thought to be difficult.

Furthermore, in coating using a sugar coating as described in JP 51-57814 A and JP 2003-125706 A, the coating is carried out by repeating the steps of liquid pouring, spreading, and drying using a sugar-coating pan. The coating therefore takes a long time, and there are concerns about increases in the sizes of the tablets themselves, and delay of disintegration.

In view of this, it could be helpful to provide a coating agent that imparts gas barrier properties to a solid preparation while keeping rapid disintegration properties of the solid preparation, and a coating formed therewith. It could also be helpful to provide a coated solid preparation that maintains the rapid disintegration properties and gas barrier properties, and does not generate cracks in the coating under humidified conditions.

SUMMARY

We discovered that an orally disintegrating coated tablet having a coating has rapid disintegration properties; shows improved physical tablet properties under humidified conditions; and has an effect of stabilizing water-unstable drugs.

We thus provide:

(1) A coating agent for a solid preparation, the coating agent comprising lactose and a swelling clay, but not comprising a water-soluble polymer, wherein the weight of the swelling clay is 20 to 50% with respect to the weight of the solid content.

(2) The coating agent according to (1), wherein the swelling clay is bentonite or aluminum magnesium silicate.

(3) The coating agent according to (1) or (2), comprising a saccharide selected from the group consisting of saccharose, trehalose, sorbitol, xylitol, maltitol, maltose, lactitol, fructose, and glucose.

(4) The coating agent according to any one of (1) to (3), wherein the weight of the lactose is 10 to 70% with respect to the weight of the solid content.

(5) The coating agent according to (3), wherein the total weight of the lactose and the saccharide is 30 to 80% with respect to the weight of the solid content.

(6) The coating agent according to any one of (3) to (5), wherein the weight of the swelling clay:the weight of the lactose=1:0.5 to 1:4, and the weight of the swelling clay:the weight of the saccharide=1:0.2 to 1:4.

(7) A coating formed with the coating agent according to any one of (1) to (6).

(8) The coating according to (7), whose disintegration occurs in an oral cavity in less than 18 seconds.

(9) A coated solid preparation comprising a solid preparation whose surface is coated with the coating according to (7) or (8).

(10) The coated solid preparation according to (9), wherein the weight of the coating is 2 to 10% with respect to the weight of the solid preparation.

(11) The coated solid preparation according to (9) or (10), which is an orally disintegrating coated tablet.

We provide a coating agent with which a decrease in the tablet hardness, an increase in the degree of friability, and a physicochemical change of the drug, due to external environmental factors such as oxygen and humidity can be suppressed by gas barrier properties of the coating, while rapid disintegration properties of the tablet can be secured; and a coating and a coated solid preparation formed with the coating agent. When an orally disintegrating tablet is coated with the coating, an orally disintegrating tablet having rapid disintegration properties in the oral cavity and having gas barrier properties, wherein cracking of the coating does not occur even under humidified conditions, can be provided.

Our coating agents, films and preparations are described below. However, this disclosure is not limited to the following examples. Unless otherwise specified, "%" represents "% by mass (w/w %)".

The coating agent for a solid preparation is characterized in that it contains lactose and a swelling clay, but does not contain a water-soluble polymer, and that the weight of the swelling clay is 20 to 50% with respect to the weight of the solid content.

The solid preparation means a preparation in a solid state, and examples of the solid preparation include supplements, nutritional functional foods, foods for specified health use, and pharmaceuticals. More specific examples of the solid preparation include tablets (including sublingual tablets and orally disintegrating tablets), capsules (including soft capsules and microcapsules), granules, fine granules, powders, balls, troches, and film preparations.

The coating formed with the coating agent may be formed on a solid preparation having another coating composed of a common water-soluble polymer, gastrosoluble or enterosoluble polymer, or the like. Alternatively, another coating composed of a common water-soluble polymer, gastrosoluble or enterosoluble polymer or the like may be formed on the surface of a solid preparation having the coating.

The coating having gas barrier properties means a coating on the surface of a solid preparation, which coating has an effect of blocking penetration of external environmental factors such as oxygen and humidity into the solid preparation during storage of the solid preparation, or an effect of blocking odors, sublimable substances and the like generated in the solid preparation to prevent their release to the outside.

The operation of forming the coating on the solid preparation comprises the step of preparing the coating agent and the step of coating the solid preparation therewith. More specifically, after preparing the coating agent for formation of the coating, the coating agent may be sprayed on, or applied to, the surface of the solid preparation, followed by removing the solvent contained in the coating agent by drying. The weight of the solid content of the coating agent means the weight after the removal of the solvent contained in the coating agent.

In the step of preparing the coating agent, the coating agent can be prepared by adding a solvent such as water, ethanol, or methanol to a swelling clay to allow swelling of the swelling clay, and then adding powders of lactose or the like to the resulting dispersion, followed by dissolving or dispersing the powder in the dispersion, or by mixing the dispersion with a liquid that is separately and preliminarily prepared by dissolving or dispersing lactose or the like. The solvents may be used individually, or as a mixture of two or more of these. Examples of the method of preparing the dispersion in which the swelling clay is swollen include a method in which the swelling clay is suspended in a dispersion medium, and the resulting suspension is stirred using a homogenizer or the like. The swelling clay is preferably in a state where it is dispersed to an extent which allows, when the dispersion is subjected to filtration, passing of the whole swelling clay through a filter paper. Examples of the filter paper to be used for the above-described filtration operation include a glass fiber filter paper GF/D (particle retention capacity, 2.7 μm; Whatman).

For the step of coating the surface of the solid preparation using the coating agent, a commonly used apparatus is employed. When the solid preparation is in granule or powders, a fluid-bed coater, a tumbling fluidized-bed coater, or the like is used. When the solid preparation is a tablet, a pan coater or the like can be used. The operating conditions are not limited, and, in a tablet having high friability, the pan may be operated at a rotation speed which is lower than usual, to allow formation of a uniform coating even on the edge portion of the tablet. Although the thickness of the coating formed varies depending on the shape and the size of the preparation, the thickness is preferably about 20 to 200 μm from the viewpoint of gas barrier properties and rapid disintegration properties.

In a solid preparation containing a drug that is very unstable in the presence of water, and when physicochemical changes occur during the coating step due to, for example, moisture absorption by a strong disintegrator, a coating agent prepared by dissolving a water-soluble substance having a high dissolution rate in ethanol alone or a mixture of ethanol and water may be used to form a thin coating (undercoat layer), and the coating may then be formed, to suppress degradation due to moisture absorption during the coating step.

Although the weight of the coating varies depending on the shape and the size of the preparation, the weight of the coating is preferably 2 to 10%, preferably 3 to 9%, more preferably 4 to 6% with respect to the weight of the solid preparation to be coated, from the viewpoint of gas barrier properties and rapid disintegration properties. When the weight of the coating is less than 2%, the preparation has insufficient gas barrier properties, while when the weight of the coating is more than 10%, the preparation has insufficient disintegration properties.

The coating formed with the coating agent can also be used as an alternative to a sugar coating for coating a tablet since the coating formed with the coating agent can achieve both rapid disintegration properties and gas barrier properties, and can be continuously produced. The coating is especially useful for coating of, among solid preparations, orally disintegrating tablets, which strongly require achievement of both rapid disintegration properties and gas barrier properties.

When a coating formed with the coating agent is to be used for a film preparation, a drug may be included in the coating agent to form a coating containing the drug, or a coating may be formed on the outer surface of the film preparation containing a drug. Since the coating can achieve both rapid disintegration properties and gas barrier properties, the film preparation can be prevented from shape changes or becoming adhesive due to moisture absorption.

An objective value of the oral disintegration time of an orally disintegrating tablet can be obtained by measuring the lengths of time required for the tablet to achieve complete disintegration by saliva in the oral cavities of three or more healthy adult male and/or female subjects who take the tablet without water or chewing the tablet, and calculating the average of the measured values. The complete disintegration of the tablet herein means the time point at which feeling of a foreign body in the oral cavity disappears. As described in Patricia Van Arnum, "Advancing ODT Technology", Pharmaceutical Technology, Vol. 3, No. 10, pp. 66-76 (published on Oct. 2, 2007), orally disintegrating tablets are generally designed such that they disintegrate in the oral cavity without water in 60 seconds. Thus, the oral disintegration time of the orally disintegrating coated tablet prepared by coating with the coating agent may be less than 60 seconds, preferably less than 50 seconds, more preferably less than 40 seconds.

The oral disintegration time of the coating can be determined by first measuring the oral disintegration time of the orally disintegrating coated tablet, and then measuring the oral disintegration time of the inner core portion of the orally disintegrating coated tablet prepared by removing the coating by cutting, followed by subtracting the disintegration time of the inner core portion from the disintegration time of the orally disintegrating coated tablet. As described in Okimoto, Jiho Inc., The Pharmaceuticals Monthly, Vol. 50, No. 11, pp. 47-55 (published on Oct. 1, 2008), the oral disintegration times of commercially available orally disintegrating tablets are from about 10 seconds to about 42 seconds. Therefore, to produce an orally disintegrating coated tablet having an oral disintegration time of less than 60 seconds, the oral disintegration time of the coating may be less than 18 seconds, preferably less than 15 seconds, more preferably less than 12 seconds. Orally disintegrating coated tablets prepared with the coating do not necessarily need to be taken without water, and may also be taken together with water.

When an orally disintegrating tablet is to be coated using the coating agent, the production method and composition of the orally disintegrating tablet as the inner core are not limited as long as the disintegration time in the oral cavity is about 1 to 42 seconds. The orally disintegrating tablet as the inner core to be used may be one produced by a conventional method in the field of pharmaceutical preparations such as direct compression, indirect compression, or molding. Examples of such production methods include a production method in which wet particles are subjected to tableting to obtain a porous tablet, a production method utilizing physicochemical properties such as crystallization of saccharides, a production method using the freeze-drying technique, a production method using a disintegrator such as crospovidone, and a production method using an external lubricant. In particular, orally disintegrating tablets prepared utilizing a disintegrator such as crospovidone are useful since they are likely to increase their volumes and to decrease their tablet hardness under humidified conditions.

The coating formed with the coating agent is unlikely to generate cracks even when the solid preparation is swollen by moisture absorption under humidified conditions. This is because the gas barrier properties of the coating suppress the swelling of the solid preparation due to the moisture absorption, and the coating maintains an appropriate strength. The presence or absence of cracks in the coating can be evaluated by leaving the coated solid preparation to stand in an atmosphere at 40° C. at 75% RH (Relative Humidity) for one day, and then observing the outer appearance of the coating.

The coating formed with the coating agent has moisture barrier properties that are equivalent to, or better than, those of commercially available coatings. The water vapor permeability of such a coating is not more than $5 \times 10^{-4}$ g·mm/cm$^2$·24 hr·atm, more preferably not more than $3 \times 10^{-4}$ g·mm/cm$^2$·24 hr·atm.

The lactose may be either an anhydride or a hydrate. The lactose is preferably a hydrate. By the use of the lactose, the productivity in the coating step can be increased, and the coating can have rapid disintegration properties and can exert gas barrier properties. The weight of the lactose is preferably 10 to 70%, preferably 30 to 70%, more preferably 40 to 70% with respect to the weight of the solid content of the coating agent.

The coating agent may further contain a saccharide selected from the group consisting of saccharose, trehalose, sorbitol, xylitol, maltitol, maltose, lactitol, fructose, and glucose. The total weight of the lactose and the carbohydrate is preferably 10 to 80%, more preferably 30 to 80%, still more preferably 50 to 80% with respect to the weight of the solid content. The coating agent especially preferably contains trehalose from the viewpoint of increasing the strength of the coating.

The swelling clay means a clay having swelling properties. Specific examples of the swelling clay include smectites such as beidellite, nontronite, saponite, hectorite, sauconite, bentonite, and aluminum magnesium silicate. Among these, bentonite and aluminum magnesium silicate are preferred. These may be commercially available products, and specific examples of the products of bentonite and aluminum magnesium silicate include KUNIPIA (registered trademark) F (Kunimine Industries Co., Ltd.), VEEGUM (registered trademark) series (granules, F, HV granules, HS granules, and K granules; Vanderbilt Minerals, LLC), Polargel (NF, T, and HV; Volclay Japan Co., Ltd.), Hectabrite, and Hectarite. One of, or a combination of two or more of, these specific examples may be used.

The swelling clay is preferably uniformly dispersed in the coating. "Uniformly dispersed" most preferably means a state where the swelling clay is dispersed as a single-layered band-shaped structure. Normally, however, in manufacturing apparatuses used for production of pharmaceuticals, separation into a single layer is difficult. In practice, the swelling clay is preferably in a state where it is dispersed as band-shaped structures that are stacked with each other to form 10 to 100 layers. The number of the layers of the band-shaped structures that are stacked with each other is preferably small. That is, when the swelling clay is uniformly dispersed in the coating, higher gas barrier properties can be obtained by a labyrinth effect of the gas.

The weight of the swelling clay may be 20 to 50%, preferably 20 to 45%, more preferably 20 to 40% with respect to the weight of the solid content of the coating agent. When the weight of the swelling clay is less than 20% with respect to the weight of the solid content of the coating agent, the film-forming properties exerted by the swelling clay is lost, and cracks are generated in the coating under humidified conditions, leading to a decrease in the gas barrier properties. When the weight of the swelling clay is more than 50% with respect to the weight of the solid content of the coating agent, a delay of the disintegration time would occur.

Preferably, in the coating agent, the weight of the swelling clay:the weight of the lactose=1:0.5 to 1:4. More preferably, the weight of the swelling clay:the weight of the lactose=1: 0.5 to 1:4, and the weight of the swelling clay:the weight of the saccharide=1:0.2 to 1:4, from the viewpoint of gas barrier properties and rapid disintegration properties. Still more preferably, the weight of the swelling clay:the weight of the lactose=1:1 to 1:3, and the weight of the swelling clay:the weight of the saccharide=1:0.2 to 1:3. Still more preferably, the weight of the swelling clay:the weight of the lactose=1:1.5 to 1:2.5, and the weight of the swelling clay:the weight of the saccharide=1:0.2 to 1:1.

The coating agent and the coating formed therewith are characterized in that they do not contain a water-soluble polymer. Without containing a water-soluble polymer, which is generally contained in conventional coating agents and coatings formed therewith, a coating having gas barrier properties can be formed while keeping rapid disintegration properties so that the coating of interest that does not generate cracks under humidified conditions can be obtained. The term "do not contain" means that a water-soluble polymer is not contained at all, or means that, even if it is contained, its amount is small and, hence, the water-soluble polymer does not play a role as a coating so that the water-soluble polymer cannot be said to be substantially contained. Examples of water-soluble polymers not contained in the coating include natural polymers such as gelatin and gum arabic; cellulose derivatives such as hydroxypropyl cellulose, hydroxypropyl methylcellulose, methylcellulose, and sodium carboxymethylcellulose; and synthetic polymers such as polyvinylpyrrolidone, polyvinyl alcohol, and polyethylene glycol (average molecular weight, 950 to 25,000).

To the coating agent and the coating formed therewith, one or more pharmaceutically acceptable additives, besides the above-described components, may be added, if necessary, as long as the desired effect is not deteriorated. Examples of the additives include corrigents, flavoring agents, coloring agents, lubricants, and light-blocking agents. Examples of the corrigents include aspartame, sucralose, saccharin sodium, dipotassium glycyrrhizinate, stevia, thaumatin, and citric acid. Examples of the flavoring agents include menthol, peppermint, lemon, lemon lime, orange, peppermint oil, and flavors. Examples of the coloring agents include tar pigments, turmeric extracts, caramel, carotene solutions, β-carotene, copper chlorophyll, and riboflavin. Examples of the lubricants include glycerol, liquid paraffin, silicone, surfactants, and waxes. Examples of the light-blocking agents include titanium oxide, red ferric oxide, yellow ferric oxide, black iron oxide, and talc. These additives are merely examples, and this disclosure is not limited by these examples. It is also possible to add one or more of these additives to the outer surface of the coating.

When the solid preparation is a tablet or a capsule, a mark(s) that can be easily identified may be printed on the outer surface of the coating using an ink by gravure offset printing, ink jet printing, UV laser printing, or the like.

When the solid preparation contains a drug, the drug does not need to be limited, and there is no restriction as long as it is a drug having a pharmacological activity. The coating agent and coatings formed therewith are especially useful for drugs that are physicochemically unstable in the presence of moisture or oxygen.

EXAMPLES

To reveal the excellent effect of our coating agents, films and preparations, we describe below various Examples. However, this disclosure is not limited by these Examples.
Measurement of Oral Disintegration Time The oral disintegration time was measured by three healthy adult male and/or female subjects. The oral disintegration time of the coating was calculated by subtracting the oral disintegration time of the core tablet from the oral disintegration time of the orally disintegrating coated tablet.
Cracks of Coating Under Humidified Conditions After storing a tablet at 40° C. at 75% RH for one day, the presence or absence of cracks in the coating was evaluated by visual observation of the tablet.
Measurement of Water Vapor Permeability Using Monolayer Film A monolayer film was formed by repeating spraying and drying of a coating agent on a release film. The water vapor permeability was measured according to a method partially modified from JIS K8123 (1994). More specifically, a portion having a uniform thickness without a pin hole was selected, and the selected portion was cut out into a circular shape having a diameter of 3.5 cm, followed by measuring the thicknesses of the monolayer film at five arbitrary positions. Subsequently, 3 g of calcium chloride (particle size, 850 to 2000 μm) was placed in an aluminum cup (30 mm diameter), and the monolayer film cut out into the circular shape and a ring for fixing the monolayer film were placed on the aluminum cup in that order, followed by placing a weight on the ring to fix the ring. Thereafter, melted paraffin wax was poured into the rim of the aluminum cup in this state. After solidification of the paraffin wax, the weight was removed, and the mass of the whole aluminum cup was measured to determine the initial mass. Subsequently, the aluminum cup was placed in an incubator at 40° C. at 75% RH, and the cup was taken out every 24 hours for measurement of its mass. According to Equation 1, the water vapor permeability coefficient was calculated. In the test for measurement of the water vapor permeability described below, r=1.5 cm, t=24 hours, and C=1 atm.

Water vapor permeability P (g·mm/cm$^2$·24 hrs·atm)= $(W \times A)/(B \times t \times C)$  Equation 1

W: mass increase in 24 hours (g)
A: average of the film thicknesses at five positions (mm)
B: permeation area $\pi r^2$ (cm$^2$)
t: time (hours)
C: atmospheric pressure (atm)

Water vapor permeabilities of OPADRY (registered trademark) AMB and EUDRAGIT (registered trademark) EPO, which are commercially available coatings having moisture barrier properties, were measured. As a result, their water vapor permeabilities were $5.2 \times 10^{-4}$ and $2.6 \times 10^{-4}$ g·mm/cm$^2$·24 hr·atm, respectively. In view of this, the moisture barrier properties of the coating were judged according to the following 2-point scale.

○: A coating with a water vapor permeability of not more than $3 \times 10^{-4}$ g·mm/cm$^2$·24 hr·atm, that is, a coating having moisture barrier properties that are equivalent to, or higher than, those of commercially available coatings having moisture barrier properties.

×: A coating with a water vapor permeability of more than $3 \times 10^{-4}$ g·mm/cm$^2$·24 hr·atm, that is, a coating having moisture barrier properties that are lower than those of commercially available coatings having moisture barrier properties.

Method of Measuring Oxygen Permeability Coefficient

The oxygen permeability coefficient of the coating formed with the coating agent for a solid preparation was measured based on the gas permeation test method by the JIS K7126-1 (2006) gas chromatography using an oxygen permeability coefficient measurement device (GTR-30XAD2G and 2700T.F; GTR Tec Corporation) at a temperature of 23±2° C. at a relative humidity of 90% (90% RH).

Reference Example 1

Production of Orally Disintegrating Tablet (Core Tablet)

To a fluid bed granulator (FLO-5; Freund Corporation), 122.6225 parts by weight (hereinafter referred to as "parts"; the same applies hereinafter unless otherwise specified) of mannitol (PEARLITOL (registered trademark); Roquette Japan), 0.0025 part of nalfurafine hydrochloride, 0.225 part of sodium thiosulfate hydrate, and 6.5 parts of crospovidone (KOLLIDON (registered trademark) CL; BASF) were loaded to produce granulated granules. Subsequently, sized granules were obtained by treatment using Comil (197S, Powrex Corporation). To 129.35 parts of the sized granules, 0.65 part of magnesium stearate (Taihei Chemical Industrial Co., Ltd.) was added to obtain granules for tableting. The granules for tableting were made into 130-mg SR tablets with a diameter of 7 mm using a tableting machine (Correct 19). The oral disintegration time of this tablet was 9 seconds.

Reference Example 2

Production of Hygroscopic Orally Disintegrating Tablet (Core Tablet)

To a fluid bed granulator, 26.3 parts of mannitol (PEARLITOL (registered trademark); Roquette Japan), 1.5 parts of hydroxypropyl cellulose (HPC-L; Nippon Soda Co., Ltd.), and 0.2 part of N-[(5R,6R,14S)-17-(cyclopropylmethyl)-4,5-epoxy-3,14-dihydroxymorphinan-6-yl]phthalimide were loaded to produce granulated granules. Subsequently, sized granules were obtained by treatment using Comil. To 28 parts of the sized granules, 94.2 parts of sorbitol powder (NEOSORB (registered trademark); Roquette Japan) and 6.5 parts of crospovidone were added, and then 1.3 parts of magnesium stearate was added to the resulting mixture, to obtain granules for tableting. The granules for tableting were made into 130-mg WR tablets with a diameter of 7 mm using a tableting machine. The oral disintegration time of this tablet was 41 seconds.

Example 1

To distilled water, 30 parts of bentonite (KUNIPIA (registered trademark) F; Kunimine Industries Co., Ltd.) was added, and the resulting mixture was stirred using a homogenizer (Polytron Model KR), followed by suction filtration using a glass fiber filter GF/D (Whatman) to obtain 3% bentonite dispersion. To the 3% bentonite dispersion (30 parts in terms of bentonite), 60 parts of lactose (lactose hydrate Pharmtose 200M, DMV) and 10 parts of trehalose (Trehalose 100; Hayashibara Co., Ltd.) were added, and distilled water was further added, followed by stirring the resulting mixture to prepare a coating agent with a solid content of 6% by weight. To a film coater (DRC-200; Powrex Corporation), 200 g of orally disintegrating tablets of Reference Example 1 were loaded, and the coating agent was sprayed thereto to prepare 133.9-mg (coverage, 3% by weight), 137.8-mg (coverage, 6% by weight), and 141.7-mg (coverage, 9% by weight) orally disintegrating coated tablets each of which is composed of a 130-mg tablet and a 3.9-mg, 7.8-mg, or 11.7-mg coating, respectively.

Example 2

Coating (coverage, 6% by weight) was carried out by the same operation as in Example 1 except that an aqueous dispersion with a solid content of 6% by weight having a composition of 20 parts of bentonite, 10 parts of lactose, and 70 parts of trehalose was used instead of the coating agent of Example 1.

Example 3

Coating (coverage, 6% by weight) was carried out by the same operation as in Example 1 except that an aqueous dispersion with a solid content of 6% by weight having a composition of 40 parts of bentonite, 50 parts of lactose, and 10 parts of trehalose was used instead of the coating agent of Example 1.

Example 4

Coating (coverage, 6% by weight) was carried out by the same operation as in Example 1 except that an aqueous dispersion with a solid content of 6% by weight having a composition of 50 parts of bentonite, 40 parts of lactose, and 10 parts of trehalose was used instead of the coating agent of Example 1.

Comparative Example 1

Coating (coverage, 6% by weight) was carried out by the same operation as in Example 1 except that an aqueous dispersion with a solid content of 6% by weight having a composition of 10 parts of bentonite, 80 parts of lactose, and 10 parts of trehalose was used instead of the coating agent of Example 1.

Comparative Example 2

Coating (coverage, 6% by weight) was carried out by the same operation as in Example 1 except that an aqueous dispersion with a solid content of 6% by weight having a composition of 60 parts of bentonite, 30 parts of lactose, and 10 parts of trehalose was used instead of the coating agent of Example 1.

Table 1 shows the performances and the coating compositions of the orally disintegrating coated tablets obtained in Comparative Examples 1 and 2, and Examples 1 to 4.

composition of 30 parts of bentonite, 60 parts of lactose, and 10 parts of polyvinyl alcohol was used instead of the coating agent of Example 1.

Comparative Example 6

The orally disintegrating tablet of Reference Example 1 was coated using the coating agent described in WO 2012/029820 A1. After adding 64 parts of bentonite to distilled water, the resulting mixture was stirred using a homogenizer, followed by performing suction filtration using a glass fiber filter paper GF/D (Whatman) to obtain 3% bentonite dispersion. To the 3% bentonite dispersion (64 parts in terms of bentonite), 27 parts of polyethylene glycol (Macrogol 6000; NOF Corporation) and 9 parts of Span 20 (Wako Pure Chemical Industries, Ltd.) were added, and the resulting mixture was stirred using a homogenizer, followed by performing suction filtration using a glass fiber filter paper GF/D (Whatman). An appropriate amount of distilled water was further added thereto, and the resulting mixture was then stirred to prepare a coating agent with a solid content weight of 4%. The coating (coverage, 7% by weight) was carried out by the same operation as in Example 1 to

TABLE 1

| | | | Comparative Example | | Example | | | |
|---|---|---|---|---|---|---|---|---|
| | | | 1 | 2 | 1 | 2 | 3 | 4 |
| Performance | Moisture barrier properties | | X | ○ | ○ | ○ | ○ | ○ | ○ | ○ |
| | Disintegration time (seconds) | Coating | 7 | 21 | 5 | 8 | 13 | 9 | 12 | 17 |
| | | Whole tablet | 17 | 33 | 14 | 18 | 24 | 19 | 21 | 27 |
| | Cracking of the coating under humidified conditions | | Yes | No | No | No | No | No | No | No |
| Composition | Swelling clay | Bentonite | 10 | 60 | 30 | 30 | 30 | 20 | 40 | 50 |
| | Lactose | Lactose | 80 | 30 | 60 | 60 | 60 | 10 | 50 | 40 |
| | Saccharide | Trehalose | 10 | 10 | 10 | 10 | 10 | 70 | 10 | 10 |
| | Weight of the coating (coverage, X %) | | 6 | 6 | 3 | 6 | 9 | 6 | 6 | 6 |
| | Swelling clay:Lactose = 1:X | | 8.0 | 0.5 | 2.0 | 2.0 | 2.0 | 0.5 | 1.3 | 0.8 |
| | Swelling clay:Saccharide = 1:X | | 1.0 | 0.2 | 0.3 | 0.3 | 0.3 | 3.5 | 0.3 | 0.2 |

Comparative Example 3

Coating (coverage, 6% by weight) was carried out by the same operation as in Example 1 except that an aqueous dispersion with a solid content of 4% by weight having a composition of 40 parts of bentonite, 50 parts of lactose, and 10 parts of polyvinyl alcohol (4-88; Merck) was used instead of the coating agent of Example 1.

Comparative Example 4

Coating (coverage, 4% by weight) was carried out by the same operation as in Example 1 except that an aqueous dispersion with a solid content of 4% by weight having a composition of 30 parts of bentonite, 50 parts of lactose, 10 parts of trehalose, and 10 parts of polyvinyl alcohol was used instead of the coating agent of Example 1.

Comparative Example 5

Coating (coverage, 6% by weight) was carried out by the same operation as in Example 1 except that an aqueous dispersion with a solid content of 4% by weight having a obtain a 139.1-mg orally disintegrating coated tablet composed of a 130-mg tablet and a 9.1-mg coating.

Comparative Example 7

Coating (coverage, 6% by weight) was carried out by the same operation as in Example 1 except that an aqueous dispersion with a solid content of 4% by weight having a composition of 40 parts of bentonite, 50 parts of lactose, and 10 parts of hydroxypropyl methylcellulose (HPMC-RW; Shin-Etsu Chemical Co., Ltd.) was used instead of the coating agent of Example 1.

Comparative Example 8

Coating (coverage, 6% by weight) was carried out by the same operation as in Example 1 except that an aqueous dispersion with a solid content of 3% by weight having a composition of 40 parts of bentonite, 50 parts of lactose, and 10 parts of copolyvidone (KOLLIDON (registered trademark) VA64; BASF) was used instead of the coating agent of Example 1.

Comparative Example 9

Coating (coverage, 6% by weight) was carried out by the same operation as in Example 1 except that an aqueous dispersion with a solid content of 4% by weight having a composition of 40 parts of bentonite, 50 parts of lactose, and 10 parts of hydroxypropyl cellulose (HPC-L; Shin-Etsu Chemical Co., Ltd.) was used instead of the coating agent of Example 1.

Comparative Example 10

Coating (coverage, 6% by weight) was carried out by the same operation as in Example 1 except that an aqueous dispersion with a solid content of 3% by weight having a composition of 40 parts of bentonite, 50 parts of lactose, and 10 parts of sodium carboxymethylcellulose (CMC-Na; Gotoku Chemical Company Ltd.) was used instead of the coating agent of Example 1.

Table 2 shows the performances and the coating compositions of the orally disintegrating coated tablets obtained in Comparative Examples 3 to 10.

Comparative Example 13

Coating (coverage, 6% by weight) was carried out by the same operation as in Example 1 except that an aqueous dispersion with a solid content of 6% by weight having a composition of 30 parts of bentonite and 70 parts of erythritol (Nikken Chemicals Co., Ltd.) was used instead of the coating agent of Example 1.

Comparative Example 14

Coating (coverage, 5% by weight) was carried out by the same operation as in Example 1 except that an aqueous dispersion with a solid content of 6% by weight having a composition of 30 parts of bentonite and 70 parts of saccharose (Frost Sugar FS-2; Nissin Sugar Co., Ltd.) was used instead of the coating agent of Example 1.

Example 5

Coating (coverage, 6% by weight) was carried out by the same operation as in Example 1 except that an aqueous

TABLE 2

|   |   |   | Comparative Example | | | | | | | |
|---|---|---|---|---|---|---|---|---|---|---|
|   |   |   | 3 | 4 | 5 | 6 | 7 | 8 | 9 | 10 |
| Performance | Moisture barrier properties | | ○ | ○ | ○ | ○ | ○ | ○ | ○ | ○ |
|   | Disintegration time (seconds) | Coating | 24 | 25 | 21 | — | 8 | 6 | 14 | 46 |
|   |   | Whole tablet | 35 | 31 | 29 | — | 19 | 17 | 25 | 57 |
|   | Cracking of the coating under humidified conditions | | No | Yes | No | Yes | Yes | Yes | Yes | No |
| Composition | Swelling clay | Bentonite | 40 | 30 | 30 | 64 | 40 | 40 | 40 | 40 |
|   | Lactose | Lactose | 50 | 50 | 60 |   | 50 | 50 | 50 | 50 |
|   | Saccharide | Trehalose |   |   | 10 |   |   |   |   |   |
|   | Water-soluble polymer | PVA | 10 | 10 | 10 |   |   |   |   |   |
|   |   | PEG6000 |   |   |   | 27 |   |   |   |   |
|   |   | HPMC |   |   |   |   | 10 |   |   |   |
|   |   | PVP VA64 |   |   |   |   |   | 10 |   |   |
|   |   | HPC-L |   |   |   |   |   |   | 10 |   |
|   |   | CMC-Na |   |   |   |   |   |   |   | 10 |
|   | Fluidizer | Span 20 |   |   |   | 9 |   |   |   |   |
|   | Weight of the coating (coverage, X %) | | 6 | 4 | 6 | 7 | 6 | 6 | 6 | 6 |
|   | Swelling clay:Lactose = 1:X | | 1.3 | 1.7 | 2.0 | 0.0 | 1.3 | 1.3 | 1.3 | 1.3 |
|   | Swelling clay:Saccharide = 1:X | | 0.0 | 0.3 | 0.0 | 0.0 | 0.0 | 0.0 | 0.0 | 0.0 |

Comparative Example 11

Coating (coverage, 3% by weight) was carried out by the same operation as in Example 1 except that an aqueous dispersion with a solid content of 6% by weight having a composition of 30 parts of bentonite and 70 parts of maltitol (MALTISORB P (registered trademark) 200; Roquette Japan) was used instead of the coating agent of Example 1.

Comparative Example 12

Coating (coverage, 5% by weight) was carried out by the same operation as in Example 1 except that an aqueous dispersion with a solid content of 6% by weight having a composition of 30 parts of bentonite and 70 parts of mannitol (PEARLITOL (registered trademark) 50C; Roquette Japan) was used instead of the coating agent of Example 1.

dispersion with a solid content of 6% by weight having a composition of 30 parts of bentonite and 70 parts of lactose was used instead of the coating agent of Example 1, to prepare 133.9-mg (coverage, 3% by weight) and 137.8-mg (coverage, 6% by weight) orally disintegrating coated tablets each of which is composed of a 130-mg tablet and a 3.9-mg or 7.8-mg coating, respectively.

Example 6

Coating (coverage, 6% by weight) was carried out by the same operation as in Example 1 except that an aqueous dispersion with a solid content of 6% by weight having a composition of 30 parts of VEEGUM (registered trademark) F (Vanderbilt Minerals, LLC) and 70 parts of lactose was used instead of the coating agent of Example 1.

Table 3 shows the performances and the coating compositions of the orally disintegrating coated tablets obtained in Comparative Examples 11 to 14, and Examples 5 and 6.

TABLE 3

|  |  |  | Comparative Example |  |  |  | Example |  |  |
|---|---|---|---|---|---|---|---|---|---|
|  |  |  | 11 | 12 | 13 | 14 | 5 | | 6 |
| Performance | Moisture barrier properties | | ○ | X | X | ○ | ○ | ○ | ○ |
| | Disintegration time (seconds) | Coating | 9 | 9 | 10 | 10 | 6 | 12 | 14 |
| | | Whole tablet | 20 | 19 | 19 | 20 | 18 | 22 | 22 |
| | Cracking of the coating under humidified conditions | | Yes | Yes | Yes | Yes | No | No | No |
| Composition | Swelling clay | Bentonite | 30 | 30 | 30 | 30 | 30 | 30 | |
| | | VEEGUM | | | | | | | 30 |
| | Lactose | Lactose | | | | | 70 | 70 | 70 |
| | Saccharide | Maltitol | 70 | | | | | | |
| | | Mannitol | | 70 | | | | | |
| | | Erythritol | | | 70 | | | | |
| | | Saccharose | | | | 70 | | | |
| | Weight of the coating (coverage, X %) | | 3 | 5 | 6 | 5 | 3 | 6 | 6 |
| | Swelling clay:Lactose = 1:X | | 0.0 | 0.0 | 0.0 | 0.0 | 2.3 | 2.3 | 2.3 |
| | Swelling clay:Saccharide = 1:X | | 2.3 | 2.3 | 2.3 | 2.3 | 0.0 | 0.0 | 0.0 |

Example 7

Coating (coverage, 6% by weight) was carried out by the same operation as in Example 1 except that an aqueous dispersion with a solid content of 6% by weight having a composition of 30 parts of bentonite, 60 parts of lactose, and 10 parts of maltitol was used instead of the coating agent of Example 1.

Example 8

Coating (coverage, 6% by weight) was carried out by the same operation as in Example 1 except that an aqueous dispersion with a solid content of 6% by weight having a composition of 30 parts of bentonite, 60 parts of lactose, and 10 parts of lactitol (Lactitol MC; Danisco Japan) was used instead of the coating agent of Example 1.

Example 9

Coating (coverage, 6% by weight) was carried out by the same operation as in Example 1 except that an aqueous dispersion with a solid content of 6% by weight having a composition of 30 parts of bentonite, 60 parts of lactose, and 10 parts of maltose (purified maltose; Hayashibara Co., Ltd.) was used instead of the coating agent of Example 1.

Example 10

Coating (coverage, 6% by weight) was carried out by the same operation as in Example 1 except that an aqueous dispersion with a solid content of 6% by weight having a composition of 30 parts of bentonite, 60 parts of lactose, and 10 parts of fructose (KRYSTAR (registered trademark) 300; Danisco Japan) was used instead of the coating agent of Example 1.

Example 11

Coating (coverage, 6% by weight) was carried out by the same operation as in Example 1 except that an aqueous dispersion with a solid content of 6% by weight having a composition of 30 parts of bentonite, 60 parts of lactose, and 10 parts of glucose (Japanese Pharmacopoeia Glucose NG-TDA; San-ei Sucrochemical Co., Ltd.) was used instead of the coating agent of Example 1.

Example 12

Coating (coverage, 6% by weight) was carried out by the same operation as in Example 1 except that an aqueous dispersion with a solid content of 6% by weight having a composition of 30 parts of bentonite, 60 parts of lactose, and 10 parts of saccharose was used instead of the coating agent of Example 1.

Example 13

Coating (coverage, 6% by weight) was carried out by the same operation as in Example 1 except that an aqueous dispersion with a solid content of 6% by weight having a composition of 30 parts of bentonite, 55 parts of lactose, 10 parts of trehalose, and 5 parts of silicone (SH200C FLUID 100CS; Dow Corning Toray Co., Ltd.) was used instead of the coating agent of Example 1.

Table 4 shows the performances and the coating compositions of the orally disintegrating coated tablets obtained in Examples 7 to 13.

TABLE 4

| | | | Example | | | | | | |
|---|---|---|---|---|---|---|---|---|---|
| | | | 7 | 8 | 9 | 10 | 11 | 12 | 13 |
| Performance | Moisture barrier properties | | ○ | ○ | ○ | ○ | ○ | ○ | ○ |
| | Disintegration time (seconds) | Coating | 9 | 11 | 10 | 10 | 9 | 9 | 9 |
| | | Whole tablet | 22 | 22 | 21 | 20 | 19 | 20 | 19 |
| | Cracking of the coating under humidified conditions | | No | No | No | No | No | No | No |

TABLE 4-continued

|  |  |  | Example |  |  |  |  |  |  |
|---|---|---|---|---|---|---|---|---|---|
|  |  |  | 7 | 8 | 9 | 10 | 11 | 12 | 13 |
| Composition | Swelling clay | Bentonite | 30 | 30 | 30 | 30 | 30 | 30 | 30 |
|  | Lactose | Lactose | 60 | 60 | 60 | 60 | 60 | 60 | 55 |
|  | Saccharide | Trehalose |  |  |  |  |  |  | 10 |
|  |  | Maltitol | 10 |  |  |  |  |  |  |
|  |  | Lactitol |  | 10 |  |  |  |  |  |
|  |  | Maltose |  |  | 10 |  |  |  |  |
|  |  | Fructose |  |  |  | 10 |  |  |  |
|  |  | Glucose |  |  |  |  | 10 |  |  |
|  |  | Saccharose |  |  |  |  |  | 10 |  |
|  | Fluidizer | Silicone |  |  |  |  |  |  | 5 |
|  | Weight of the coating (coverage, X %) |  | 6 | 6 | 6 | 6 | 6 | 6 | 6 |
|  | Swelling clay:Lactose = 1:X |  | 2.0 | 2.0 | 2.0 | 2.0 | 2.0 | 2.0 | 1.8 |
|  | Swelling clay:Saccharide = 1:X |  | 0.3 | 0.3 | 0.3 | 0.3 | 0.3 | 0.3 | 0.3 |

Example 14

A small amount of distilled water was added to 90 parts of polyethylene glycol (Macrogol 6000; NOF Corporation) and 10 parts of hydroxypropyl methylcellulose (HPMC E; Shin-Etsu Chemical Co., Ltd.) to dissolve these materials. Ethanol was added to the resulting solution such that precipitation did not occur, to obtain a coating agent A. To distilled water, 30 parts of bentonite was added, and the resulting mixture was stirred using a homogenizer, followed by suction filtration using a glass fiber filter GF/D (Whatman) to obtain 3% bentonite dispersion. To the 3% bentonite dispersion (30 parts in terms of bentonite), 60 parts of lactose and 10 parts of trehalose were added, and the resulting mixture was stirred to prepare a coating agent B with a solid content of 6% by weight. To a film coater (DRC-200; Powrex Corporation), 200 g of hygroscopic orally disintegrating tablets of Reference Example 2 were loaded, and the coating agent A was sprayed thereto to obtain 131.3-mg (coverage, 1% by weight) orally disintegrating undercoated tablets each composed of a 130-mg tablet and a 1.3-mg coating. Further, the coating agent B was sprayed to obtain 139.16-mg (coverage, 6% by weight) orally disintegrating coated tablets each composed of a 131.3-mg tablet and a 7.86-mg coating. The oral disintegration time of the orally disintegrating undercoated tablet was 42 seconds; the oral disintegration time of the orally disintegrating coated tablet was 52 seconds; and the oral disintegration time of the coating was 10 seconds.

Evaluation of Moisture Barrier Properties of Coating, Using Tablets

The orally disintegrating tablet (core tablet) obtained in Reference Example 2 and the orally disintegrating coated tablet of Example 14 were stored at 25° C. at 70% RH, and then the moisture barrier properties of the coating was evaluated based on the rate of increase with respect to the total weight.

Figure 1:
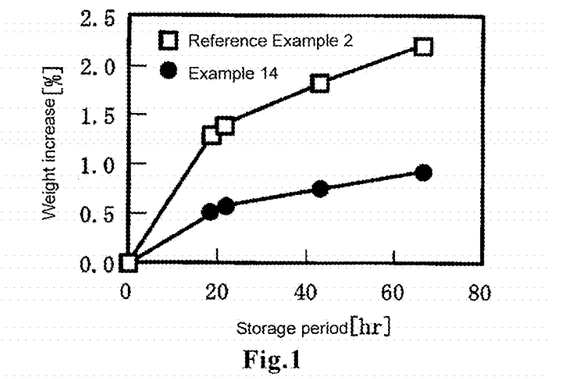
FIG. 1 is a diagram showing changes in the weight increase rate with time during the storage period in Reference Example 2 and Example 14, wherein the weight at 0 hr of the storage period in Reference Example 2 and Example 14 is regarded as 100%.

FIG. 1 shows changes in the weight increase rate with time during the storage period in Reference Example 2 and Example 14, wherein the total weight at 0 hr of the storage period in Reference Example 2 and Example 14 is regarded as 100%.

Example 15

To a coating pan, 25 g of sodium valproate tablets (DEPAKENE TABLET (registered trademark) 100 mg; Kyowa Hakko Kirin Co., Ltd.) and 225 g of placebo tablets (for increasing the volume) were loaded, and the sodium valproate tablets were coated with the coating agent of Example 1 (coverage, 5% by weight).

Figure 2:
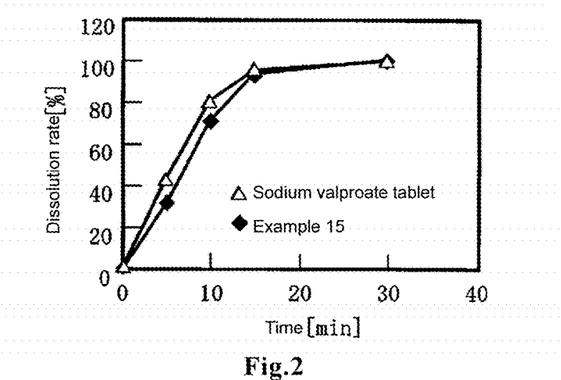
FIG. 2 is a diagram showing changes in the dissolution rates with time of uncoated sodium valproate tablets and the coated sodium valproate tablets obtained in Example 15.

Dissolution profiles of uncoated sodium valproate tablets and the coated sodium valproate tablets obtained in Example 15 were studied. The dissolution test was carried out according to the second method of the Japanese Pharmacopoeia, 15th Edition, "Dissolution Test". In this method, distilled water was used as a test liquid, and the tablets were loaded into 900 mL of the test liquid. The resulting solution was collected with time, and subjected to quantification test under the following HPLC conditions. The changes in the dissolution rate with time obtained as a result are shown in FIG. 2.

HPLC Conditions

Mobile phase: 50 mM sodium dihydrogen phosphate/acetonitrile=5/5 (v/v)
Column: Devolosil ODS-5 (4.6×150 mm)
Detection wavelength: 210 nm As shown in FIG. 2, the coated sodium valproate tablets obtained in Example 15 were found to show a dissolution profile equivalent to that of sodium valproate tablets.

Uncoated sodium valproate tablets and the coated sodium valproate tablets obtained in Example 15 were stored at 25° C. at a relative humidity of 60%, and their changes in the external appearance were observed. As a result, the sodium valproate tablets (core tablets for Example 15) showed deliquescence after one day of the storage due to moisture absorption, while Example 15 showed no change in the external appearance even after six weeks of the storage.

Comparative Example 15

Using the coating agent described in WO 2010/113841 A1, the orally disintegrating tablets of Reference Example 1 were coated. In distilled water, 30 parts of PVA and 40 parts of lactose were dissolved, and 27 parts of titanium oxide (HA-R; Freund Corporation) and 3 parts of red ferric oxide (Kishi Kasei Co., Ltd.) were further added thereto, followed by stirring the resulting mixture using a homogenizer. After further adding distilled water thereto, the mixture was stirred to obtain a coating agent with a solid content of 10% by weight. To a film coater, 200 g of orally disintegrating tablets produced in Reference Example 1 were loaded, and the coating agent was sprayed thereto to prepare 133.9-mg orally disintegrating coated tablets (coverage, 3% by weight) each of which is composed of a 130-mg tablet and a 3.9-mg coating.

Comparative Example 16

The orally disintegrating tablet of Reference Example 1 was coated with a coating agent prepared using talc, which is a non-swelling inorganic compound, instead of a swelling clay. To distilled water, 70 parts of lactose and 30 parts of talc (Victory Light SK-C; Shokozan Mining Co., Ltd.) were added, and the resulting mixture was stirred using a homogenizer, followed by filtration through a 150-μm sieve, to prepare a coating agent with a solid content weight of 4.5%. The coating (coverage, 3% by weight) was carried out by the same operation as in Example 1 to obtain a 134.4-mg orally disintegrating coated tablet composed of a 130-mg tablet and a 4.4-mg coating.

Comparative Example 17

The orally disintegrating tablet of Reference Example 1 was coated with the coating agent described in WO 2012/147873 A1. To distilled water, 50 parts of trehalose and 50 parts of talc were added, and the resulting mixture was stirred using a homogenizer, followed by filtration through a 150-μm sieve, to prepare a coating agent with a solid content weight of 5%. The coating (coverage, 3% by weight) was carried out by the same operation as in Example 1 to obtain a 134.4-mg orally disintegrating coated tablets composed of a 130-mg tablet and a 4.4-mg coating.

Table 5 shows the performances and the coating compositions of the orally disintegrating coated tablets obtained in Comparative Examples 16 and 17.

TABLE 5

| | | | Comparative Example | |
|---|---|---|---|---|
| | | | 16 | 17 |
| Performance | Moisture barrier properties | | x | x |
| | Disintegration time (seconds) | Coating | 6 | 5 |
| | | Whole tablet | 21 | 18 |
| | Cracking of the coating under humidified conditions | | Yes | Yes |
| Composition | Non-swelling inorganic compound | Talc | 30 | 50 |
| | Lactose | Lactose | 70 | |
| | Saccharide | Trehalose | | 50 |
| | Weight of the coating (coverage, X %) | | 3 | 3 |
| | Swelling clay:Lactose = 1:X | | — | — |
| | Swelling clay:Saccharide = 1:X | | — | — |

Measurement of Tablet Hardness

The orally disintegrating tablets obtained in Reference Example 1 (core tablet), and the orally disintegrating coated tablets obtained in Example 1 (coverage, 6% by weight) and Comparative Example 15 (coverage, 3% by weight) were subjected to measurement of the tablet hardness immediately after the production, and the tablet hardness after storage at 40° C. at 75% RH for 5 days, using a hardness tester (Portable Checker PC-30; Okada Seiko Co., Ltd.) (Table 6).

TABLE 6

Effect to suppress a decrease in the tablet hardness

| | Reference Example 1 | Example 1 (coverage, 6%) | Comparative Example 15 |
|---|---|---|---|
| Tablet hardness (immediately after production) | 45 | 42 | 53 |
| Tablet hardness (after storage at 40° C. at 75% RH for 5 days) | 6 | 31 | 13 |

Measurement of Degree of Friability

The orally disintegrating tablets obtained in Reference Example 1 (core tablet), and the orally disintegrating coated tablets obtained in Example 1 (coverage, 6% by weight) were subjected to measurement of the degree of friability immediately after the production, and the degree of friability after storage at 40° C. at 75% RH for 5 days, according to the test method for the degree of friability described in page F-131 of the Japanese Pharmacopoeia, 15th Edition, General Notices (Table 7).

TABLE 7

Effect to improve the friability resistance

| | Reference Example 1 | Example 1 |
|---|---|---|
| Degree of friability (immediately after production) | 0.15% | 0.04% |
| Degree of friability (after storage at 40° C. at 75% RH for 5 days) | 0.80% | 0.05% |

Measurement of Oxygen Permeability Coefficient

The oxygen permeability coefficients of the coatings formed with the coating agents of Example 1 and Comparative Examples 15 and 17 are shown in Table 8.

TABLE 8

Measurement of oxygen permeability coefficient

Unit: $cm^3 \cdot mm/cm^2 \cdot 24\ hrs \cdot atm$

| | |
|---|---|
| Example 1 | $4.0 \times 10^{-5}$ |
| Comparative Example 15 | 65.7 |
| Comparative Example 17 | Unmeasurable because of too much permeation |

As a result, Example 1 was found to have better gas barrier properties against oxygen compared to Comparative Examples 15 and 17.

Example 16

The coating agent of Example 1 was repeatedly sprayed and dried on an olopatadine film preparation (olopatadine hydrochloride film 2.5 mg "Maruho"; Kyukyu Pharmaceutical Co., Ltd.) to form a coating (thickness, 24 μm) on both sides.

Example 17

The coating agent of Example 1 was repeatedly sprayed and dried on a loratadine film preparation (Loratadine OD Film "KN"; Kobayashi Kako Co., Ltd.) to form a coating (thickness, 24 μm) on both sides. The disintegration time of this coated film preparation was 22 seconds, and the disintegration time of the coating portion was 5 seconds.

Evaluation of Moisture Barrier Properties of Coating, Using Film Preparations

Figure 3:
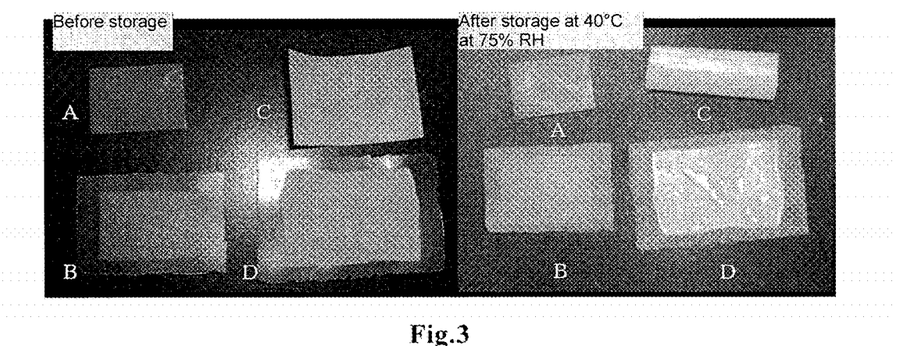
FIG. 3 is a diagram showing photographs for comparison of the external appearances of an uncoated olopatadine film preparation (A), loratadine film preparation (C), Example 16 (B), and Example 17 (D), which photographs were taken before storage, and after storage at 40° C. at a relative humidity of 75% for 1 day.

The uncoated olopatadine film preparation (A), loratadine film preparation (C), Example 16 (B), and Example 17(D) were stored at 40° C. at a relative humidity of 75%, and their changes in the external appearance were observed. FIG. 3 shows photographs for comparison of their external appearances, which photographs were taken before storage, and after storage for 1 day.

As a result, A and C showed shape changes and adhesiveness in the film preparations due to moisture absorption, while B and D showed no change in their external appearances, and could be easily handled.

As shown in Tables 1 to 5, the coatings formed with the coating agents for a solid preparation according to Examples 1 to 13, each of which contains lactose and a swelling clay, but does not contain a water-soluble polymer, wherein the weight of the swelling clay is 20 to 50% with respect to the weight of the solid content, were found to have better rapid disintegration properties compared to the coatings formed with the formulations of Comparative Examples 1 to 14 and Comparative Examples 16 and 17, and found not to generate cracks in the coating even when they are stored under humidified conditions at 40° C. at 75% RH. As shown in Table 6, those coatings were found to be capable of remarkably suppressing decreases in the tablet hardness of orally disintegrating tablets due to moisture absorption. As shown in Table 7, those coatings were found to be capable of remarkably increasing the friability resistance. As shown in FIG. 1, those coatings were found to have remarkable gas barrier properties, and to be capable of keeping sufficient stability during handling of solid preparations that are unstable in the presence of water. As shown in FIG. 3, those coatings were found to be capable of suppressing adhesiveness and shape changes in film preparations due to moisture absorption, and securing ease of handling. And, as shown in Table 8, since a coating formed with our coating agent has remarkable oxygen barrier properties, the coating agent was suggested to be useful also for solid preparations that are unstable not only in the presence of water, but also in the presence of oxygen.

INDUSTRIAL APPLICABILITY

The coating agent for a solid preparation, and coatings and coated solid preparations formed therewith, can improve ease of handling of solid preparations that are unstable in the presence of water, and allow one-dose packaging of orally disintegrating tablets to which one-dose packaging had been inapplicable. Thus, in particular, therapeutic effects of pharmaceutical preparations can be enhanced by improvement of drug compliance of patients.

The invention claimed is:

1. A coating agent for a solid preparation comprising lactose and a swelling clay, but not comprising a water-soluble polymer, wherein the weight of said swelling clay is 20 to 50% with respect to the weight of the solid content.

2. The coating agent according to claim 1, wherein said swelling clay is bentonite or aluminum magnesium silicate.

3. The coating agent according to claim 1, comprising a saccharide selected from the group consisting of saccharose, trehalose, sorbitol, xylitol, maltitol, maltose, lactitol, fructose, and glucose.

4. The coating agent according to claim 1, wherein the weight of said lactose is 10 to 70% with respect to the weight of the solid content.

5. The coating agent according to claim 3, wherein the total weight of said lactose and said saccharide is 30 to 80% with respect to the weight of the solid content.

6. The coating agent according to claim 3, wherein the weight of said swelling clay:the weight of said lactose=1:0.5 to 1:4, and the weight of said swelling clay:the weight of said saccharide=1:0.2 to 1:4.

7. A coating formed with the coating agent according to claim 1.

8. The coating according to claim 7, whose disintegration occurs in an oral cavity in less than 18 seconds.

9. A coated solid preparation comprising a solid preparation whose surface is coated with the coating according to claim 7.

10. The coated solid preparation according to claim 9, wherein the weight of said coating is 2 to 10% with respect to the weight of said solid preparation.

11. The coated solid preparation according to claim 9, which is an orally disintegrating coated tablet.

12. The coating agent according to claim 2, comprising a saccharide selected from the group consisting of saccharose, trehalose, sorbitol, xylitol, maltitol, maltose, lactitol, fructose, and glucose.

13. The coating agent according to claim 2, wherein the weight of said lactose is 10 to 70% with respect to the weight of the solid content.

14. The coating agent according to claim 3, wherein the weight of said lactose is 10 to 70% with respect to the weight of the solid content.

15. The coating agent according to claim 4, wherein the weight of said swelling clay:the weight of said lactose=1:0.5 to 1:4, and the weight of said swelling clay:the weight of said saccharide=1:0.5 to 1:4.

16. The coating agent according to claim 5, wherein the weight of said swelling clay:the weight of said lactose=1:0.5 to 1:4, and the weight of said swelling clay:the weight of said saccharide=1:0.5 to 1:4.

17. A coated solid preparation comprising a solid preparation whose surface is coated with the coating according to claim 8.

18. The coated solid preparation according to claim 10, which is an orally disintegrating coated tablet.

* * * * *

UNITED STATES PATENT AND TRADEMARK OFFICE
CERTIFICATE OF CORRECTION

PATENT NO. : 10,022,331 B2  
APPLICATION NO. : 15/129153  
DATED : July 17, 2018  
INVENTOR(S) : Takaki et al.

Page 1 of 1

It is certified that error appears in the above-identified patent and that said Letters Patent is hereby corrected as shown below:

In the Claims

<u>In Column 22,</u>
At Lines 45 and 49, please change "1:0.5" to -- 1:0.2 --.

Signed and Sealed this  
Eleventh Day of September, 2018

Andrei Iancu  
*Director of the United States Patent and Trademark Office*